United States Patent [19]

Tarasova et al.

[11] 3,965,130

[45] June 22, 1976

[54] METHOD FOR PREPARING ERGOSTEROL AND UBIQUINONE-9 IN A SINGLE PROCESS

[76] Inventors: Nina Vasilievna Tarasova, Krasnaya Presnya, 45, kv. 12; Elena Abramovna Obolnikova, Astrakhansky pereulok, 19, korpus 2, kv. 37; Alexandr Dmitrievich Gololobov, Belomorskaya ulitsa, 20, kv. 101; Gleb Ivanovich Samokhvalov, ulitsa M. Ulyanovol, 3, korpus 3, kv. 53; Sergei Vladimirovich Chepigo, Lenigradsky prospekt, 74, korpus 2a, kv. 9; Galina Ivanovna Ivanova, Leninsky prospekt, 93, korpus 4, kv. 130; Vladimir Vasilievich Imshenetsky, Novokuznetsky pereulok, 11/13, kv. 8; Vera Mikhailovna Kulikova, Ulyanovskaya ulitsa, 52a, kv. 4, all of Moscow, U.S.S.R.

[22] Filed: Dec. 20, 1974

[21] Appl. No.: 534,667

[52] U.S. Cl. .................... 260/396 R; 260/397.25
[51] Int. Cl.$^2$ ................ C07C 45/24; C07C 49/73; C07J 9/00

[58] Field of Search ............... 260/396 R, 397.25

[56] References Cited
UNITED STATES PATENTS

| | | | |
|---|---|---|---|
| 1,733,009 | 10/1929 | Gams et al. | 260/397.25 |
| 2,730,536 | 1/1956 | Feeney | 260/397.25 |
| 2,753,362 | 7/1956 | Owades et al. | 260/397.25 |
| 2,794,035 | 5/1957 | Hummel | 260/397.25 |
| 2,837,540 | 6/1958 | Buehler | 260/397.25 |
| 2,865,934 | 12/1958 | Fisher | 260/397.25 |
| 3,006,932 | 10/1961 | Green et al. | 260/397.25 |

*Primary Examiner*—Vivian Garner
*Attorney, Agent, or Firm*—Steinberg and Blake

[57] ABSTRACT

A method for simultaneous preparation of ergosterol and ubiquinone-9 in a single process, characterized in that a biolipid fraction, isolated from a biomass of yeast, for example Candida, is used in the process.

This fraction is hydrolyzed with a solution of alkali in alcohol, and unsaponifiable components are then extracted. The extract is evaporated to precipitate ergosterol, while the mother liquor is passed through a chromatographic column to isolate ubiquinone-9. According to the invention, both end products are obtained in a single process.

5 Claims, No Drawings

METHOD FOR PREPARING ERGOSTEROL AND UBIQUINONE-9 IN A SINGLE PROCESS

This invention relates to methods of preparing biologically potent substances, and more particularly it relates to a method for preparing ergosterol and ubiquinone-9 at the same time.

Said products are synthesized in the process of cultivation of yeast, for example those belonging to genera Candida, Torula, and others.

Ergosterol is a high-molecular sterol. When isolated in crystalline form it is an intermediate product used for preparing vitamins D, including its active metabolites, and, in the chemicopharmaceutical industry, for preparing steroid hormones.

Ubiquinones belong to the class of 2,3-dimethoxy-5-methylbenzoquinones having, in the position 6, lateral chains consisting of isoprenoid links differing in number, and designated, accordingly, $Q_1-Q_{10}$. Substances belonging to this class have co-enzymatic activity in electron-transporting systems and participate both in the energetic and constructive metabolic processes of a living cell. Animal cells are characterized by the presence of ubiquinones-10 and -9, and in plant and microbeal cells ubiquinones can be synthesized with shorter isoprenoid chains.

At the present time, there is evidence of efficacy of ubiquinone preparations in treating cardiovascular insufficiency and alimentary and genetic dystrophy in animals. Ubiquinones are also effective in cases of anemia associated with protein metabolic disorders in man.

Known in the prior art is a method for industrial preparation of ergosterol from yeast belonging to genus Saccharomyces which is used for preparing vitamin $D_2$. The process comprises the following steps. Pressed yeast is processed with ethyl alcohol and the extract is filtred. The yeast coagulate undergoes alkaline hydrolysis with heating and continuous stirring with subsequent separation of an insoluble residue by filtration, evaporation of the alcoholic solution, and purification of crude ergosterol; the purification process comprises triple affination and re-crystallization of the affinated product (cf L. O. Schneidman, 'Vitamin Production', "Pischevaia promyshlennost" Publishers, 1973).

U.S. Pat. No. 2,874,171 covers a process in which the whole biomass of the yeast is hydrolyzed in an alkali-butanol mixture with autoclaving at a temperature of 120°C.

Disadvantages of the known methods are as follows:
1. The starting material, yeast Saccharomyces, grown on carbohydrate media, is expensive.
2. Both methods are based on hydrolysis to be conducted under critical conditions, which makes it impossible to isolate the other end product, ubiquinone.
3. The concentration of ergosterol in the crude material is low (27-34 per cent). As a result of after purification, the concentration increases to 9-95 per cent, but the purification process involves labour-consuming triple affination and recrystallization.

Ubquinone-9 is known to be produced by the culture Candida tropicalis Kp-33 on composite media containing mineral salts, a narrow fraction of n-alkanes ($C_{10}-C_{13}$), the precursor of the aromatic ring (p-hydroxy-benzoic acid), biogenic stimulants (malic acid and corn-steep liquor) and a detergent (cf. J-Ferm. Technol. 48, No. 9, 533-556, 1970. S. Chimizu, A. Tanaka, and S. Fukui). The object of studies of the Japanese investigators was supersynthesis of ubiquinone-9 rather than the development of a method for preparing it. Although remarkable progress has been attained in biosynthesis of ubiquinone-9, the process still suffers from the following disadvantages.

1. A specially selected producer agent, capable of supersynthesis of ubiquinone-9, but having low rate of propagation, is used in the process.
2. Supersynthesis of ubiquinone-9 by the culture Candida tropicalis Kp-233 is conducted with expensive nutrient media containing a precursor of the aromatic ring, biogenic stimulants, detergents, and a narrow fraction of n-alkanes ($C_{10}-C_{13}$).
3. Isolation of ubiquinone-9 requires hydrolysis of the whole mass which makes it impossible to utilize its proteinous component in animal husbandry.

Said method has only been realized on a laboratory scale, and there is no information on its industrial efficiency.

Literature contains no data on methods in which ergosterol and ubiquinone could be produced simultaneously.

It is therefore an object of this invention to provide a new method for preparing ergosterol and ubiquinone-9 from the products of synthesis of yeast that would makes it possible to obtain both products simultaneously in a single process.

These and other objects are attained in a method for preparing ergosterol and ubiquinone-9, which, according to the invention, comprises hydrolysis of a biolipid fraction isolated from a biomass of yeast, producing ergosterol and ubiquinone-9, with an alcoholic solution of alkali, in the presence of an antioxidant preventing oxidation of ergosterol and ubiquinone-9; extraction of unsaponifiable components from the hydrolysis mixture; evaporation of the extract to precipitate ergosterol crystals; separation of crystalline ergosterol from the mother liquor; removal of the remaining extracting agent from the mother liquor; adsorption chromatographic isolation of the oily product, remaining after the removal of the extracting agent, and isolation of ubiquinone-9.

The term 'biolipid fraction' is here used to denote the fraction isolated from the biomass of various yeasts capable of producing ergosterol and ubiquinone-9, containing fat-soluble cell components.

In order to avoid possible nucleophilic substitution of the methoxy group in the molecule of ubiquinone-9 by the alkoxy group, lower aliphatic alcohols, preferably methyl alcohol, should be used in the hydrolysis of the biolipid fraction. It is preferably to use potassium hydroxide as the alkali metal hydroxide in the alcohol-alkali hydrolysis since this alkali permits less stringent conditions of the process. The concentration of potassium hydroxide should be from 8 to 12 per cent. Higher concentration of the alkali decreases the yield of the end products.

According to the invention, any substances that prevent oxidation of ergosterol and ubiquinone-9 can be used as the antioxidant in the hydrolysis. For example, pyrogallol, Santoquin, butyl oxytoluene, and other suitable antioxidants can be used.

The quantity of the antioxidant may vary depending on the particular substance used. For example, the quantity of pyrogallol is 1-3 per cent of the weight of the biolipid fraction.

The hydrolysis is recommended to be carried out with boiling for 30–45 minutes. This time is sufficient to obtain maximum yields of the end products.

According to the invention, the hydrolyzed mixture is extracted to isolate unsaponifiable components. Any suitable organic solvents inert with respect to ergosterol and ubiquinone-9, can be used as the extracting agents. n-hexane, petroleum ether, diethyl ether, benzene, and others, can be used, for example. Diethyl ether is the preferred solvent, since it produces smaller quantities of stable emulsions during the extraction process.

According to the invention, the obtained extract is evaporated to precipitate crystals of ergosterol, that are separated from the mother liquor. The remaining quantities of the extracting agent are removed from the mother liquor and the resultant oily product is separated by adsorption chromatography on a column packed, for example, with aluminium oxide.

Given below is a detailed description of the proposed method.

The biolipid fraction is used as the starting material for preparing ergosterol and ubiquinone-9.

Any biolipid fraction isolated from yeast, producing ergosterol and ubiquinone-9, for example, strain Candida, can be used in this process.

The biolipid fraction, alcoholic solution of alkali, and said antioxidant are loaded into a reactor provided with a stirrer, and a reflux condenser. The mixture is heated to boiling with stirring. The hydrolyzed mixture is cooled, diluted with water, and extracted with said extracting agent, for example, by the counter-current method, or with the use of mixing-setting tanks. During the extraction process, the unsaponifiable components are transferred into the extracting agent, while the saponified water-soluble components are separated with the aqueous phase and discarded. The separated extract is washed with water to neutral and evaporated in a vat until crystalline ergosterol is precipitated.

The vat residue is unloaded from the apparatus, cooled, and ergosterol is isolated by any suitable method, for example, by filtration, centrifuging, etc. The separation ergosterol is washed with petroleum ether and re-crystallized from a mixture of ethyl alcohol - benzene. The purity of the thus obtained ergosterol is 95–98 per cent.

The remaining mother liquor contains ubiquinone-9. In order to recover it, the mother liquor is evaporated to remove the remaining quantities of the extracting agent to obtain an oily liquid which is passed through a chromatographic column packed with an adsorbing material, for example, alumina, silicic acid, silica gel, etc. The yellow band of the column packing, containing ubiquinone-9, is washed with a mixture of petroleum ether and diethyl ether. The eluate contains ubiquinone-9. The solvent is then removed from the eluate and the residue is recrystallized from ethyl alcohol or acetone. The purity of the thus obtained ubiquinone-9 is 95–100 per cent.

If the biolipid fraction, isolated from the yeast grown on media contain n-alkanes, is used in the process, the latter includes additional steps in which the alkanes are removed before passing through the chromatographic column by dissolving the oily residue in acetone and freezing out.

The proposed invention has certain advantages over the known method, which are as follows:

1. The invention provides conditions for simultaneous preparation of two substances, namely, ergosterol and ubiquinone-9 in a single process, the purity of the end products being as high as 100 per cent. The yield of ergosterol is 10–15 g/kg of the biolipid fraction, and the yield of ubiquinone-9 is 1.2–1.7 g/kg of the biolipid fraction.

2. The method proposed in this invention utilizes industrial strains of yeast that are used in preparing fodder and edible protein, for example Candida strains, while specially selected strains of the same genus are required to produce ubiquinone-9 according to the known method.

3. The invention utilizes the biolipid fraction obtained from yeast, irrespective of the method by which the yeast is grown. In some branches of industry the biolipid fraction is a waste material, as is the case with preparing protein-vitamin concentrates from Candida yeast grown on media containing n-alkanes. The separation of the biolipid fraction from the biomass improves the quality of the proteinous component of fodder concentrates, which in turn prolongs the time period within which the concentrates can be stored.

Thus, the separation and utilization of the biolipid fraction makes it possible to intensify on the whole the microbiological process of preparing protein-vitamin concentrates.

For better understanding of the invention, the following examples of specific embodiments thereof are given by way of illustration.

EXAMPLE 1

The biolipid fraction is prepared as follows.

Yeast Candida guillermondi HI-4 is grown with aeration on a nutrient medium containing sources of nitrogen, phosphorus, microelements, and also a mixture of pure n-alkanes ($C_{11}$–$C_{23}$) as a source of carbon. The biomass is separated from the culture fluid and dried. The biolipid fraction is extracted from 70 kg of dry biomass with 280 liters of petroleum ether. The extraction is continued for 6–8 hours. The extract is separated from the proteinous concentrate and evaporated in vacuum at a temperature of 40°C. The yield of the biolipid fraction is 7 kg (sp.gr. 0.96).

The composition of the biolipid fraction is as follows (wt.%)

| hydrocarbons | 72 | free fatty acids | 15 |
| phospholipids | 30 | ubiquinone | 0.18 |
| glycerides | 43 | balance | |
| styrenes | 1.5 | unidentified impurities | |

The whole of the obtained quantity of the biolipid fraction is placed in a reactor provided with a reflux condenser, a heater, and a stirrer. A solution containing 1.4 kg of potassium hydroxide and 0.14 kg of pyrogallol in 14 liters of methyl alcohol is added into the reactor. The mixture is boiled with stirring for 45 minutes, then cooled to 15°–20°C, and transferred into an extractor, into which 35 liters of water are added. The unsaponifiable fraction of the biolipids is extracted three times with 28, 14 and 14 liters of diethyl ether respectively. The extracts are washed with water to neutral reaction, the ether is evaporated until the volume of the liquid is about 2 liters. The vat residue is cooled to about −5°C, and kept at this temperature for 3 hours. The precipitated ergosterol is washed with petroleum ether and dried in vacuum at 45°–50°C to prepare 98.8 g of ergosterol having a purity of 85 per cent. After recrystallization from a mixture of ethyl ether and benzene (4:1), the yield of product is 79 g; it contains 98 per cent of ergosterol. The melting point is 156°–159°C. The product is colorless crystals; when melted together with a sample of ergosterol obtained from yeast *Saccharomyces cerevisiae*, the melting point is not lowered.

$\lambda_{max}^{ethanol}$ 262, 271, 282, 293 nm.

After separation of ergosterol, the solvent is removed completely from the remaining mother liquor. The residue is frozen out at a temperature of −6°C with two ml of acetone to separate it from higher n-alkanes. The latter are filtered, and the solution is evaporated to dryness. The remaining oily product is separated on a chromatographic coloumn packed with aluminium oxide. The band of the absorbent containing ubiquinone is washed out with a mixture of petroleum ether and diethyl ether. The eluate containing ubiquinone-9 is evaporated at a temperature not above 35°C. The residue is crystallized from absolute ethyl alcohol. The precipitated ubiquinone-9 is separated by filtration and dried. The yield of ubiquinone-9 is 9.5 g. The yellow crystals contain 97.9 per cent of the main product. The melting point is 43.6°–44.4°C.

$\lambda_{max}^{ethanol}$ (oxid) 272 nm, $E_{1cm}^{1\%}$ 180;

$\lambda_{max}^{ethanol}$ 290 nm (red), $E_{1cm}^{1\%}$ 50.5.

Mass-spectrum, M/e: 794 (M$^+$), 796 (2+M)$^+$, 779 (M-15)$^+$, 235, 197.

EXAMPLE 2

The biolipid fraction is isolated from crude yeast *Candida tropicalis* H-30 by extraction with acetone with subsequent transfer of the fat-soluble components into n-hexane or petroleum ether. 7.5 g of the biolipid fraction are obtained from 170 g of yeast (moisture content 81 per cent). The biolipids are then processed to isolate ergosterol and ubiquinone-9 as described in Example 1. The yield of the process is 78 mg of ergosterol, containing 97.3 per cent of the main product. The yield of ubiquinone-9 is 6.9 mg, the content of the main product being 99.2 per cent.

What is claimed is:

1. Method of recovering both ergosterol and ubiquinone-9, in a single process from a biomass of a yeast which produces both ergosterol and ubioquinone-9, which comprises extracting the biolipid fraction from the biomass of said yeast containing ergosterol and ubiquinone-9 by means of a solvent for said biolipid fraction, separation said biolipid fraction from said solvent, hydrolyzing said biolipid fraction with a solution of alkali in lower aliphatic alcohol in the presence of an antioxidant which prevents oxidation of ergosterol and ubiquinone-9, extracting the unsaponifiable components from the thus hydrolyzed mixture by means of an organic solvent therefor, evaporating the thus obtained extract to crystallize out ergosterol, separating the precipitated ergosterol crystals from the mother liquor, removing the remaining solvent from the mother liquor, thus obtaining an oily product, and subjecting said oily product to adsorption on a chromatographic column, eluting and recovering the ubiquinone-9 from the eluate.

2. A method as claimed in claim 1, wherein a solution of potassium hydroxide in methyl alcohol is used for hydrolysis.

3. A method as claimed in claim 1, wherein pyrogallol is used as the antioxidant.

4. A method as claimed in claim 1, wherein the extraction of said unsaponifiable components from the hydrolyzed mixture is performed with diethyl ether.

5. Method according to claim 1 wherein said yeast is of the genera Candida.

* * * * *